(12) United States Patent
Xam-Mar Mangrane

(10) Patent No.: US 10,470,852 B2
(45) Date of Patent: Nov. 12, 2019

(54) SCREW, TOOL AND ASSEMBLY FOR DENTAL IMPLANTOLOGY

(71) Applicant: Esteban Xam-Mar Mangrane, Lleida (ES)

(72) Inventor: Esteban Xam-Mar Mangrane, Lleida (ES)

(*) Notice: Subject to any disclaimer, the term of this patent is extended or adjusted under 35 U.S.C. 154(b) by 9 days.

(21) Appl. No.: 14/443,872

(22) PCT Filed: Mar. 27, 2013

(86) PCT No.: PCT/ES2013/070210
§ 371 (c)(1),
(2) Date: May 19, 2015

(87) PCT Pub. No.: WO2014/076332
PCT Pub. Date: May 22, 2014

(65) Prior Publication Data
US 2015/0289953 A1    Oct. 15, 2015

(30) Foreign Application Priority Data

Nov. 19, 2012  (BR) .......................... 10 2012 029369

(51) Int. Cl.
| | |
|---|---|
| *A61C 8/00* | (2006.01) |
| *A61C 1/08* | (2006.01) |
| *B25B 15/00* | (2006.01) |
| *F16B 23/00* | (2006.01) |

(52) U.S. Cl.
CPC .......... *A61C 8/0089* (2013.01); *A61C 1/084* (2013.01); *A61C 8/0022* (2013.01); *A61C 8/0068* (2013.01); *A61C 8/0074* (2013.01); *B25B 15/005* (2013.01); *F16B 23/003* (2013.01)

(58) Field of Classification Search
CPC ... A61C 8/0089; A61C 8/0068; A61C 8/0074; A61C 8/0022; B25B 15/005; F16B 23/003
USPC .................................................. 433/172–176
See application file for complete search history.

(56) References Cited

U.S. PATENT DOCUMENTS

| | | | |
|---|---|---|---|
| 2005/0287497 A1 | 12/2005 | Carter | |
| 2009/0151519 A1* | 6/2009 | Monyem | B25B 13/06 81/124.4 |
| 2010/0211118 A1* | 8/2010 | Christen | A61B 17/8635 606/312 |

(Continued)

FOREIGN PATENT DOCUMENTS

| | | |
|---|---|---|
| EP | 1 810 641 A1 | 7/2007 |
| EP | 2 444 024 A1 | 4/2012 |

(Continued)

OTHER PUBLICATIONS

International Search Report of PCT/ES2013/070210 dated Sep. 18, 2013.

(Continued)

*Primary Examiner* — Matthew M Nelson
(74) *Attorney, Agent, or Firm* — Sughrue Mion, PLLC

(57) ABSTRACT

The invention relates to a screw, a tool and a system for dental implantology, forming a fixing system and the components thereof to be used in a dynamic pillar assembly. Said dynamic pillar assembly is used in the production of prostheses on dental implants in human implantology in order to fix screws at an angle.

5 Claims, 11 Drawing Sheets

(56) References Cited

U.S. PATENT DOCUMENTS

| | | | | |
|---|---|---|---|---|
| 2011/0098715 A1* | 4/2011 | Laubert | ............... | A61B 17/861 606/104 |
| 2011/0143316 A1* | 6/2011 | Olson | ................. | A61C 8/0089 433/147 |
| 2011/0306014 A1* | 12/2011 | Conte | .................... | A61C 8/005 433/173 |
| 2012/0035669 A1* | 2/2012 | Jackson | ............ | A61B 17/7032 606/305 |
| 2013/0006314 A1* | 1/2013 | Mueller | ............ | A61B 17/8042 606/328 |
| 2014/0081333 A1* | 3/2014 | Jackson | ............ | A61B 17/7031 606/257 |
| 2014/0100616 A1* | 4/2014 | Shipp | ................ | A61B 17/7082 606/86 A |

FOREIGN PATENT DOCUMENTS

| | | |
|---|---|---|
| ES | 2 335 510 T3 | 3/2010 |
| WO | 2006/024680 A1 | 3/2006 |

OTHER PUBLICATIONS

Written Opinion of the International Searching Authority of PCT/ES2013/070210 dated Sep. 18, 2013.
International Preliminary Report on Patentability of PCT/ES2013/070210 dated Apr. 22, 2015.

* cited by examiner

DIME-1        DIMA-1

RCP-1        RDP-1

SCREW, TOOL AND ASSEMBLY FOR DENTAL IMPLANTOLOGY

OBJECT OF THE INVENTION

The present invention relates to a screw, a tool and a system for dental implantology, forming a fixing system and the components thereof to be used in a dynamic pillar assembly or in mechanized structures or structures sintered by CadCam laser. Said dynamic pillar assembly or mechanized structure are used in the production of prostheses on dental implants in human implantology in order to fix screws at an angle.

The object of the present invention is to increase the screwing angle of the dynamic pillar or mechanized structure, providing advantages for improving the safety of the screwing system of the dynamic pillar or mechanized structure of the implant, correcting a large number of problems, increasing the durability, increasing the number of solutions for resolving aesthetic and functional problems, reducing the probability of the tool decoupling from the head of the screw during use thereof, increasing flexibility of use and maintaining the cost with respect to the screws and screwdrivers used in the prior art.

BACKGROUND OF THE INVENTION

In the international patent application, WO2006/0247680, from the same applicant, a system comprising a guide tube, a base, a screw and a screwdriver for acting on a dynamic pillar implant is described. The dynamic pillar, which is the object of said invention, comprises two independent pieces constituting the base and the guide tube, or chimney, which are connected to each other by means of an articulation, of which independent pieces the base has a semi-spherical configuration and the chimney has, at the end of the coupling to the base, a complementary configuration, the articulation of which allows the chimney to form a maximum angle of 25° with the base, which is coupled by means of a screw to the longitudinal bore of the implant introduced into the bone, the pieces of which, base and chimney, following casting, form one single metallic piece having the desired angulation, which allows the correct positioning thereof, overcoming any incorrect angular arrangement of the implant in the bone, screwing said structure, at the corrected angulation, directly into the implant.

According to the cited invention, the combination of said pieces, articulated base and chimney, provide a freedom of movement of between 0° and 25° for positioning in relation one another at the desired angle prior to proceeding with the casting. Another object of said invention is the screwdriver (tool for coupling/decoupling by means of a screw of the dynamic pillar of said invention to the implant introduced into the bone), which has a protrusion in the form of a nut head which functions as a tip of the screw for coupling the dynamic pillar to the implant, by means of the complementary housing provided on the head of the screw and which has a substantially spherical configuration defined by a succession of faces constructed by surfaces in the form of interpolation of truncated spherical radii at both ends.

Although the guide tube or chimney has fulfilled the requirement of orientating the screwdriver together with the screw, their characteristics limit the tightening process of said screw at a maximum angle of 25°, producing disadvantages in serving a limited number of applications and solutions to problems, with high probability that the thread will be lost, with low probability of solving aesthetic and functional problems and less flexibility of use.

The screws and the screwdriver of said invention have the following problems, which the present invention solves:
a) Limited angle up to a maximum of 25 degrees;
b) As the spherical tip of the screwdriver has a hexagonal form and the female part of the head of the screw also has the same form, the tightening only occurs by means of the perfect engagement of both;
c) The probability of the screwdriver decoupling from the head of the screw is very high;
d) Reduces the probability of the hexagon of the head of the screw losing its hexagonal form, a very high probability in the currently known systems, which causes the tip of the screwdriver to rotate in its interior, impeding the correct functioning of the assembly during the tightening thereof.

At the same time, in the prior art there exist different fixing devices for the joining of the two elements, in particular, screws which have heads with different geometries which work with tips of complementary screws for the screwing of the screw to another element by means of a thread. In the prior art, no fixing device with a head at one end and a thread at the opposite end is known which allows the actuation thereof by means of a screwdriver in such a way that between the axis of the tip of the screwdriver and the head of the screw where the tip of the screwdriver is introduced there exists a degree greater than 25° and allows the tightening with sufficient guarantees.

DESCRIPTION OF THE INVENTION

The invention was developed to overcome the limitations and disadvantages of the guide tube or chimney, the screws and the screwdrivers of the prior art by means of constructive modifications which improve the safety of the screwing system of the dynamic pillar, allowing screwing at angles greater than 25 degrees and consequently correcting a greater number of angulation problems of the implants, increasing the number of solutions to problems of poor positioning in the area of the implants, increasing the durability of the screw and the screwdriver whilst displaying less wear due to a larger contact surface and better engagement and coupling between both and allowing greater flexibility of the male and female engagements, providing advantages such as the greater number of solutions for resolving aesthetic and functional problems, less probability of the screwdriver losing contact or decoupling from the screw during the threading, less probability of the geometric form of the head of the screw losing its form, greater flexibility of use and the same costs in relation to the screws and keys of the prior art.

Therefore, a first object of the present is a fixing device with a thread and a head for receiving a tool. The hexalobular form has greater tangent radii in the exterior area than the known hexalobular systems, which allows the resistance and inclination of the screw and screwdriver assembly to be increased.

A second object of the present invention is a tool.

A third object of the present invention is an assembly for implantology, which has a base, a chimney or guide tube and a fixing device.

The present invention is also applicable to metallic structures for implants produced by means of the CadCam process, not exclusively for dynamic pillar assemblies. The structures of the prosthesis produced by means of a casting process require the dynamic pillar as a base piece for modelling the structure in wax and then carrying out the casting, fixing the pillar in its correct position. On the other hand, the metallic structures formed by means of a CadCam process do not require the dynamic pillar since the structure is designed by computer and a tool machine mills said structure using only the screw and screwdriver of the system for the screwing thereof at angulation.

DESCRIPTION OF THE FIGURES

To complement the description and with the aim to provide a better understanding of the characteristics of the invention, a set of figures is included, in which the following is depicted in an illustrative and non-limiting character.

PREFERRED EMBODIMENT OF THE INVENTION

The dynamic pillar assembly comprises two independent pieces which are the base (B) which is coupled to an implant and the guide tube or chimney (T) which is coupled to the base and via which an aesthetic material is inserted, these being connected to each other by means of an articulation with a semi-spherical configuration provided at the free end of the base (B) and a complementary configuration provided at the end of the coupling of the chimney with a cylindrical configuration, said guide tube (T) having a single access hole on the side opposite to that of the articulation with the base (B) which allows the introduction of a screw (P) and a screwdriver (C).

The base (B) and the guide tube (T) which may be made of any material, metallic or plastic, form a single structure, having the form required for the buccal anatomy of the patient after having been anatomically modelled and subsequently cast, having the desired angulation in the interior of the structure to be situated in the correct position on the implant, although the latter is incorrectly inserted. Said single metallic structure is coupled by means of the base (B), already cast, by means of a retaining device, specifically a screw, which is threaded on the longitudinal thread of the implant which is in the bone, accessing the head of said screw by means of the hole existing in the chimney, said metallic structure being covered by an aesthetic material which simulates the tooth. The metallic structure may also be obtained by means of a CadCam process, in which the structure is designed by computer or subsequently manufactured directly by a tool machine or sintered by a laser.

Figure 1:
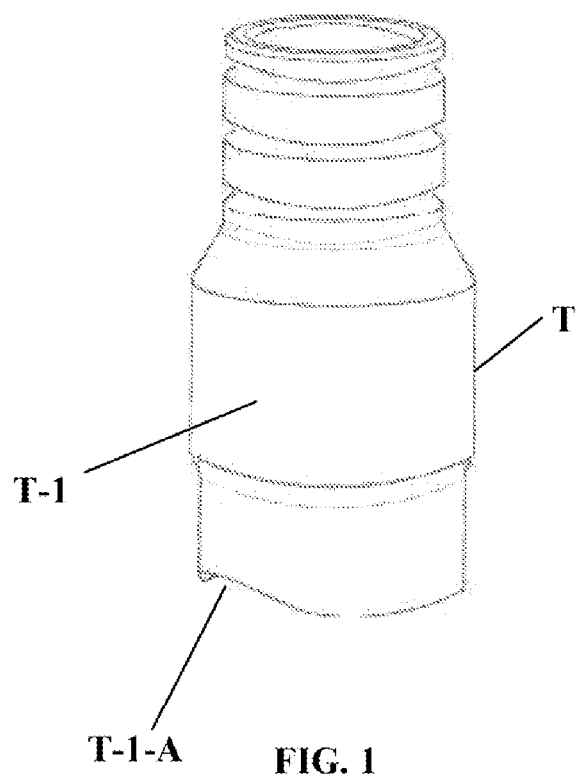
FIG. 1 shows a frontal perspective view of a guide tube of the dynamic pillar.
Figure 2:
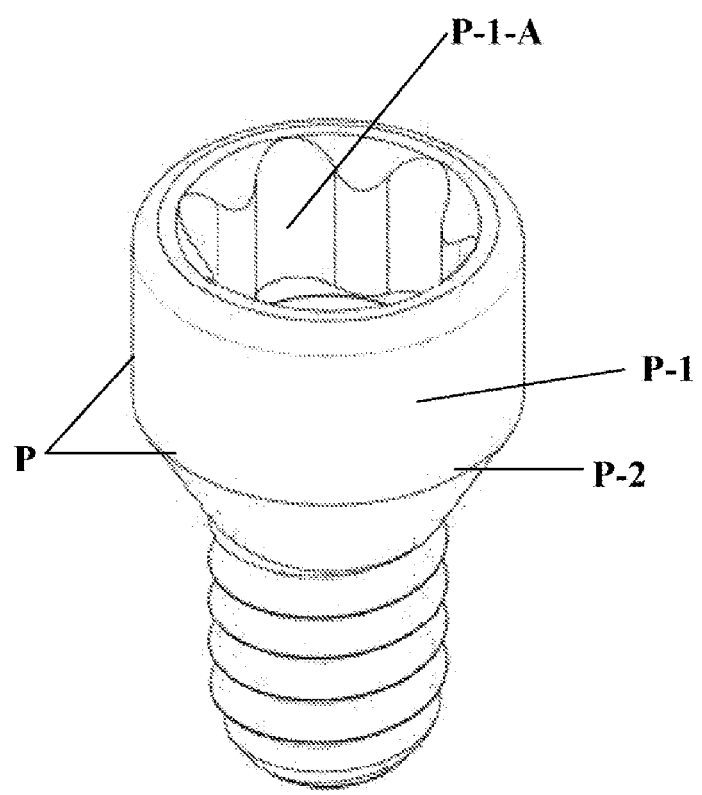
FIG. 2 shows the frontal perspective view of a screw of the dynamic pillar.
Figure 3:
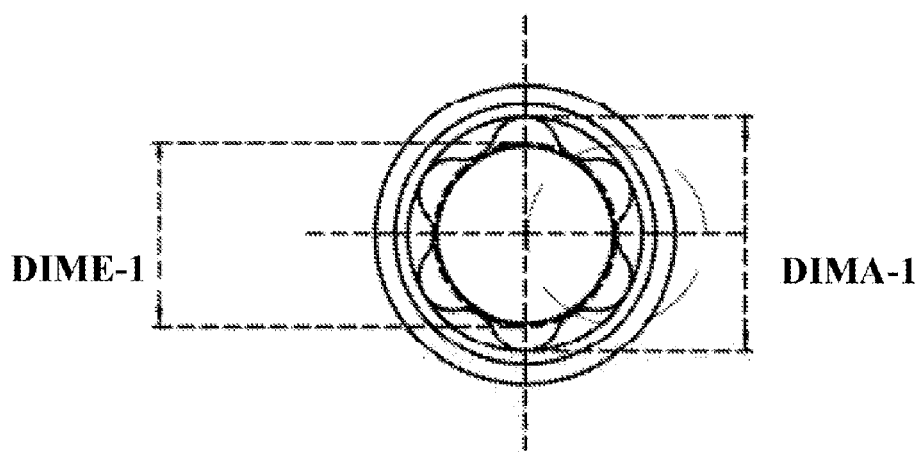
FIG. 3 shows the upper view of the screw of the dynamic pillar.
Figure 4:
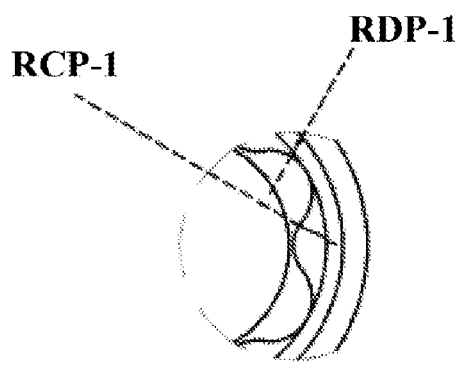
FIG. 4 shows the upper view with greater detail of the depressions and peaks of the screw of the dynamic pillar.
Figure 5:
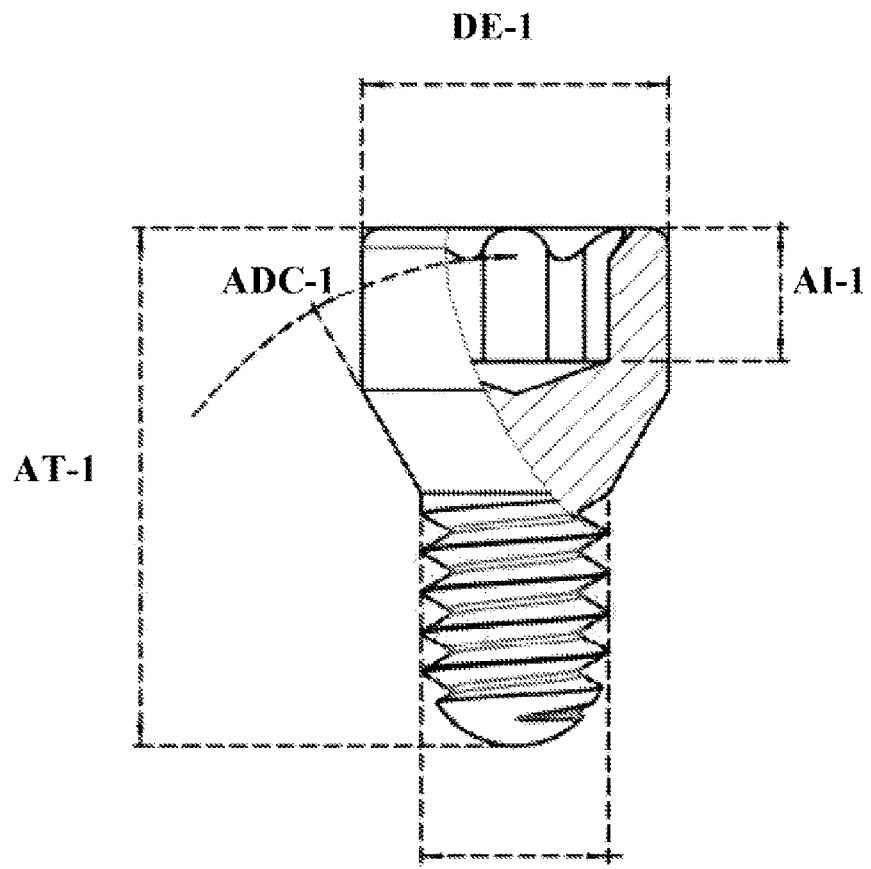
FIG. 5 shows the frontal and sectional rear view of the screw of the dynamic pillar.
Figure 6:
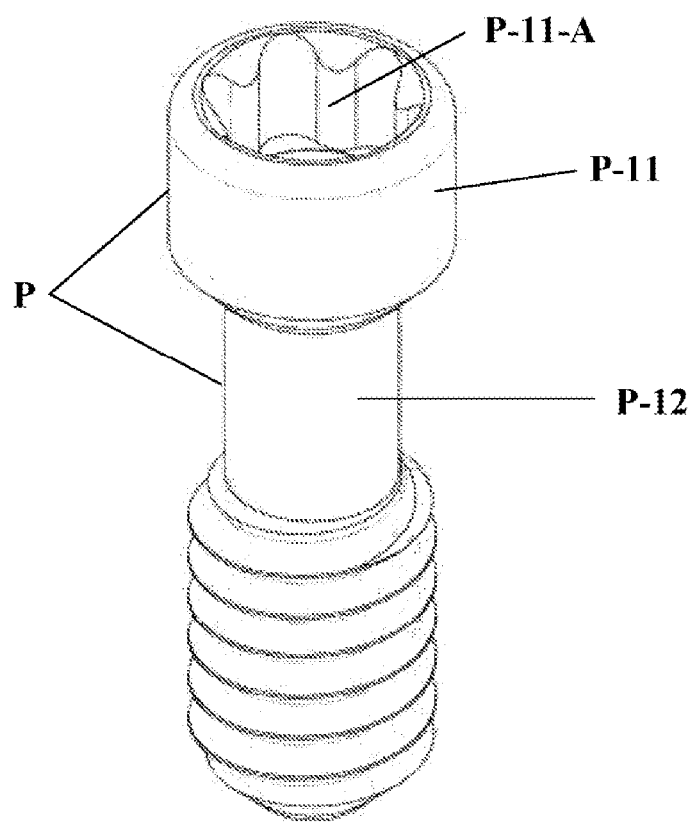
FIG. 6 shows the frontal perspective view of an alternative of the screw of the dynamic pillar.
Figure 7:
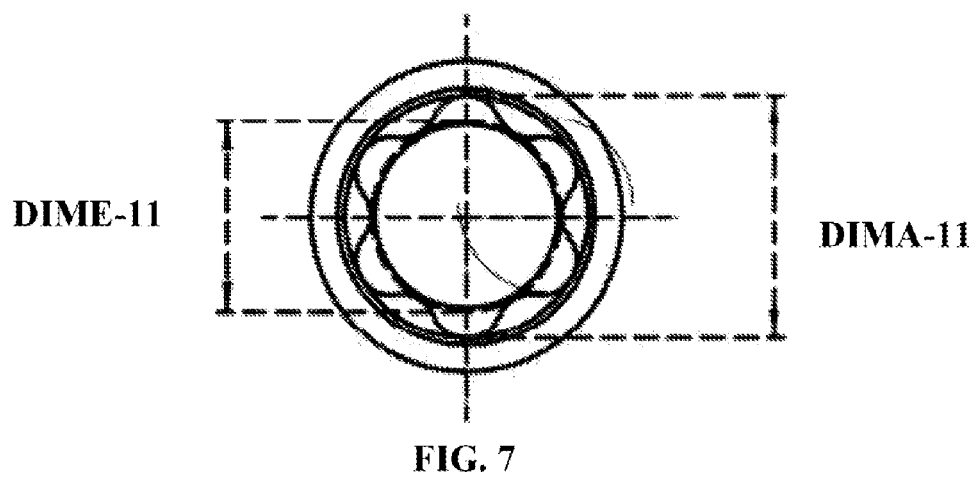
FIG. 7 shows the upper view of the screw of the previous figure.
Figure 8:
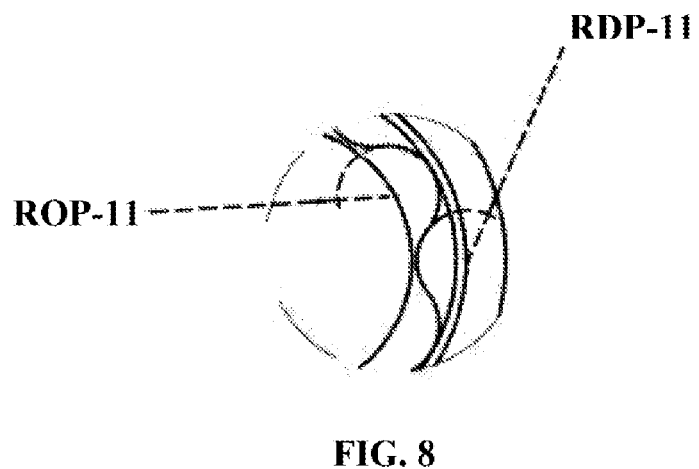
FIG. 8 shows the upper view with greater detail of the depressions and peaks of the screw of the previous figure.
Figure 9:
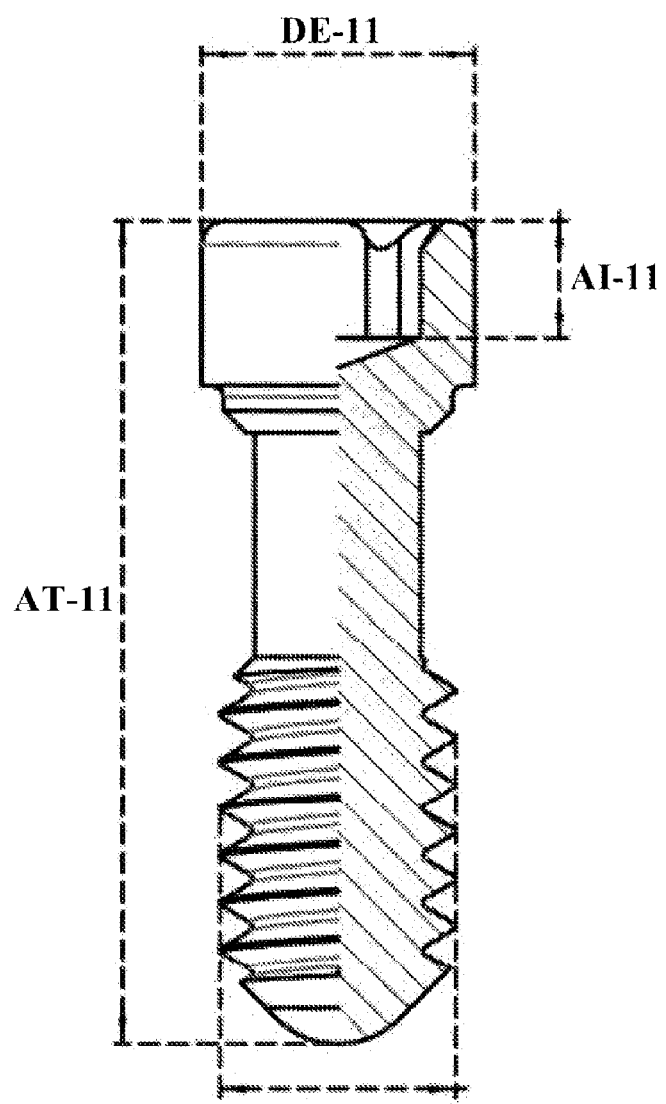
FIG. 9 shows the frontal and sectional rear view of the screw of the previous figure.

In accordance with FIG. 1, a guide tube (T) of the dynamic pillar assembly comprises a body (T-1) in staggered cylindrical and conical form with improvements to the semi-circular body (T-1) at the lower edge of the side which allows a maximum inclination of 30°, preferably 28°, in the case of the dynamic pillar due to the design of the height of the semi-sphere of the dynamic pillar base, and up to 35°, preferably 30°, in the case of an angled channel obtained by a CadCam process, adjusting the design of the pitch of the screw in each case according to the length of the screw.

In accordance with FIGS. 2 to 5, the screw (P) of the dynamic pillar comprises a head (P-1) in cylindrical form followed by a body (P-2) in tapered form with its lower ends having a thread for the threading thereof with a conical seat and in semi-spherical form in the lower part. The head (P-1) has an internal part (P-1-A) with female hexalobular form with a circular center and six depressions and six peaks alternating on the periphery, the head (P-1) having an external diameter (DE-1) which varies between 1.8 mm and 2.7 mm, greater internal diameter (DIMA-1) which varies between 1.3 and 2.4 mm, smaller internal diameter (DIME-1) which varies from 1.0 to 2.0 mm, an internal height of (AI-1) which varies from 0.5 to 1.5 mm, a radius of the depression (RDP-1) which varies from 0.15 to 0.35 mm, a radius of the peak (RCP) which varies from 0.15 to 0.35 mm, an angle of the cone (ADC-1) which varies from 25 to 65 degrees and a total height (AT-1) which varies from 2 to 15 mm.

In accordance with FIGS. 6 to 9, an alternative screw (P) of the dynamic pillar of the present industrial design is shown which may comprise a head (P-11) in cylindrical form, with an upright seat and a body (P-12) in cylindrical form with a lower end with a cylindrical body of smaller diameter than the head and followed by a thread of greater external diameter than the cylindrical body finished in a semi-spherical form in the lower part. The head (P-11) has an internal part (P-11-A) with a hexalobular form with a circular center and six depressions and six peaks alternating on the periphery, the head (P-11) having an external diameter (DE-11) which varies from 1.8 mm to 2.7 mm in diameter, a greater internal diameter (DIMA-11) which varies from 1.3 to 2.4 mm, a greater internal diameter (DIME-11) which varies from 1.0 to 2.0 mm, an internal height (AI-11) which varies from 0.5 to 1.5 mm, a radius of the depression (RDP-11) which varies from 0.15 to 0.35 mm, a radius of the peak (RCP-11) which varies from 0.15 to 0.35 mm and a total height (AT-11) which varies from 2 to 15 mm.

Due to an exclusive hexalobular geometric design, with exterior radii with greater resistant section and adapted to the adjustment between the screw and the screwdriver, an inclination of up to 35 effective degrees, preferably 30°, is allowed for applying the tightening torque and loosening of the screw.

Figure 10:
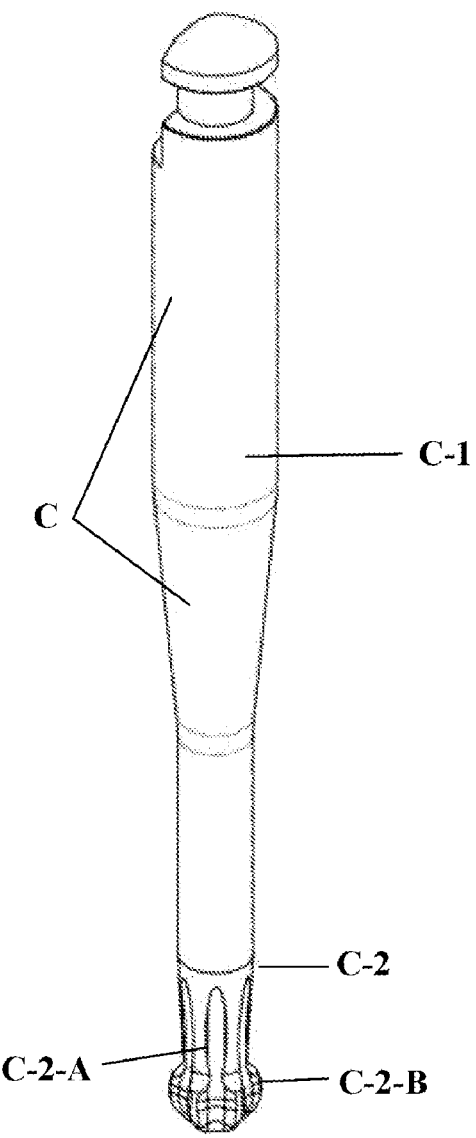
FIG. 10 shows the perspective view of a screwdriver of the dynamic pillar.
Figure 11:
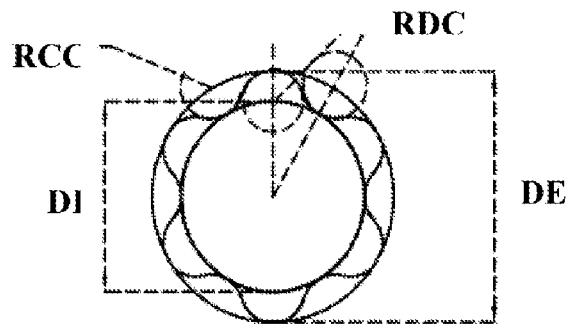
FIG. 11 shows the upper view of the screwdriver.
Figure 12:
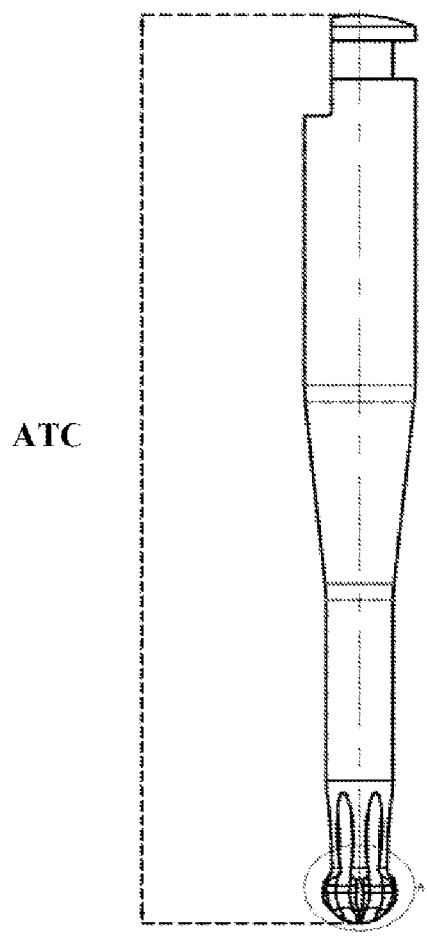
FIG. 12 shows a lateral view of the screwdriver.

In accordance with FIGS. 10 to 12, the screwdriver (C) of the dynamic pillar comprises a body (C-1) in cylindrical and tapered form with an upper part preferably in a "T" form with a curved upper face and a cut face with a cut extended into the upper cylinder, intermediate part in tapered form and lower part with grooves and curves with improvement to the tip (C-2) in semi-spherical form with curved holes (C-2-A)

and protrusions (C-2-B) forming a male hexalobular type screwdriver, with an external diameter (DE) which varies from 1.3 to 2.4 mm, an internal diameter (DI) which varies from 1.0 to 2.0 mm, the radius of the depression (RCD) which varies from 0.15 to 0.35 mm, the radius of the peak (RCC) which varies from 0.15 to 0.35 mm and a total height (ATC) which varies from 18 to 35 mm.

The adjustment between the screw and the screwdriver is carried out by means of tangent radii adapted between said screw and screwdriver, which allows torque at an inclination of up to 35°, preferably 30° to be applied.

Figure 13:
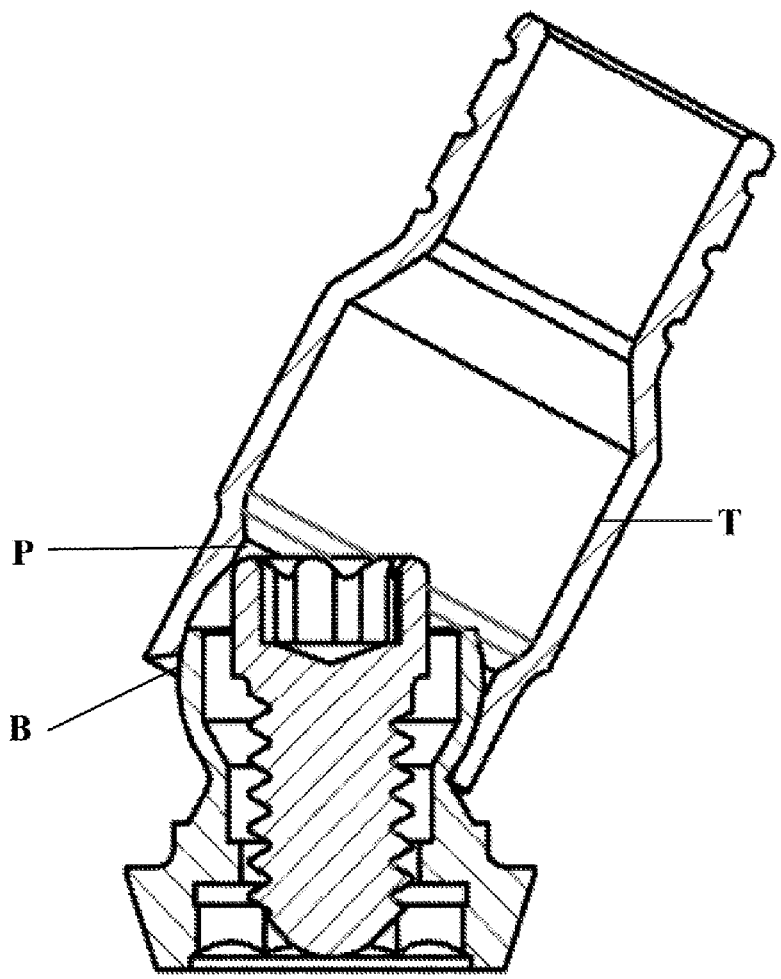
FIG. 13 shows a section of the assembly, base, chimney and screw of the pillar.
Figure 14:
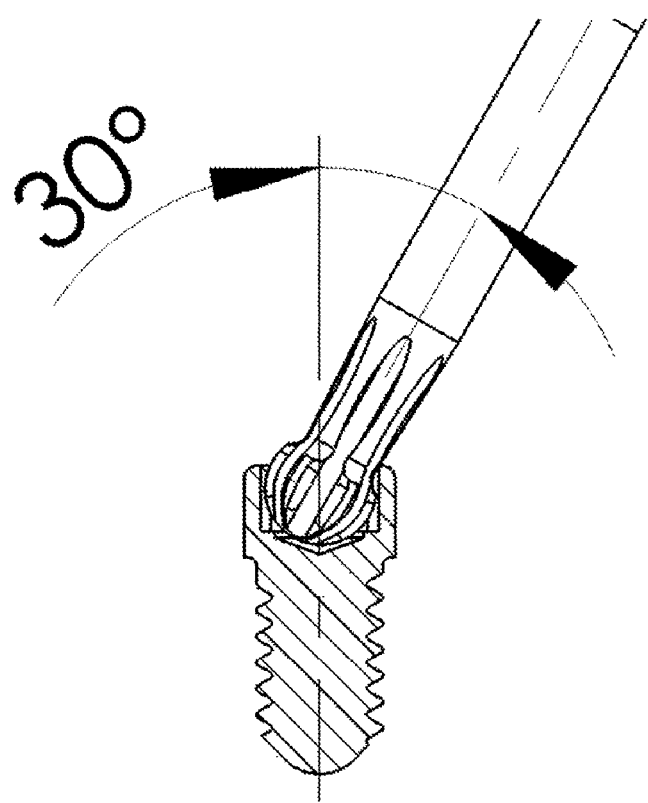
FIG. 14 shows a section of the screw with the tip of the screwdriver introduced into the head of the screw.

By means of the previous elements, and in particular by means of coupling and connection of the screw and the screwdriver, it is possible to achieve an articulation which allows the guide tube or chimney (T) to form an angle from 0° to 35°, preferably 30°, in relation to the base (B), as is observed in FIGS. 13 and 14.

At the same time, the procedure for correcting the incorrectly positioned implants by means of the dynamic pillar and the elements of the present invention, comprises the following steps:
Obtaining an impression of the mouth of the patient who has the implant;
Obtaining a working model of the mouth of the patient with the exact position of the implants which the patient has;
Screwing, using the screw (P) and the screwdriver, (C) a dynamic pillar, with its base (B) and guide tube (T), into a replica of the implant in the working model and positioning the guide tube (T) at a desired angulation in relation to the base (B);
Fixing the position between the base (B) and the guide tube (T) at a previously defined angulation;
Anatomical modelling of the form of the client on the base (B) and the guide tube (T);
Unscrewing, using the screw (P) and the screwdriver (C), the modelled assembly formed by the base (B) and guide tube (T) from the replica of the implant;
Casting the modelled assembly of the base (B) and guide tube (T) for obtaining a single metallic structure;
Screwing, using the screw (P) and the screwdriver (C), the metallic structure into the implant of the mouth of the patient;
Covering said metallic structure with aesthetic material, which simulates the tooth.

At the same time, the procedure for correcting incorrectly positioned implants by means of CadCam and the elements of the present invention comprises the following steps:
Obtaining an impression of the mouth of the patient who has the implant;
Obtaining a working model of the mouth of the patient with the exact position of the implants which the patient has;
Scanning the model in order to reproduce it in 3D;
Modelling the future metallic structure using the CAD software;
Sending the design of the structure to a tool machine which mills the structure using the commands from the CAM software;
Screwing, using the screw (P) and the screwdriver (C), the metallic structure into the implant of the mouth of the patient; and
Covering said metallic structure with aesthetic material, which simulates the tooth.

As mentioned previously, instead of using a milling machine, it is possible to use a laser sintering machine, which executes the commands from the CAM software.

The invention claimed is:

1. A screw for a dynamic pillar for dental implantology, the screw comprising a head at one end and a thread at an opposite end, wherein the head of the screw has an internal part (P-1-A) with female hexalobular form with a circular center and six circular depressions and six circular peaks alternating on the periphery, each circular depression defined by a same depression radius and each circular peak define by a same peak radius, said hexalobular form allowing an inclination of between 0° and 35° for the application of a tightening torque by a screwdriver; and
wherein, for each of the six circular depressions, a curve defining the circular depression is along the same depression radius and for each of the six circular peaks, a curve defining the circular peak is along the same peak radius;
wherein the head of the screw has an external diameter (DE-1) from 1.8 mm to 2.7 mm, a greater internal diameter (DIMA-1) from 1.3 to 2.4 mm, a smaller internal diameter (DIME-1) from 1.0 to 2.0 mm, and an internal height (A1-1) from 0.5 to 1.5 mm; and
wherein the depression radius is from 0.15 to 0.35 mm and the peak radius is from 0.15 to 0.35 mm.

2. The screw according to claim 1, further comprising a mating screwdriver for driving the screw, the screwdriver comprising a male tip (C-2) in semi-spherical form with curved inlets and protrusions (C-2-B) defining a male hexalobular form, said hexalobular form defined by alternating circular depressions and circular peaks, each circular depression defined by a same depression radius and each circular peak define by a same peak radius, said hexalobular form allowing an inclination of between 0° and 35° for the application of a tightening torque on a screw for the dynamic pillar for dental implantology; and
wherein the hexalobular form has a maximum external diameter (DE) from 1.3 mm to 2.4 mm, a maximum internal diameter (DI) in a range of 1.0 to 2.0 mm, radius of the depression (RCD) in a range of 0.15 to 0.35 mm, and a radius of the peak (RCC) in a range of 0.15 to 0.35 mm, and wherein the screwdriver has a total height (ATC) in a range of 18 to 35 mm.

3. The screw according to claim 1, wherein a cone (ADC-1) is formed between the thread and the head of the screw and an angle of the cone is from 25 to 65 degrees.

4. A screwdriver, for a dynamic pillar for dental implantology, comprising a male tip (C-2) having a body in partial spherical form with curved inlets and protrusions (C-2-B) defining a male hexalobular form, said hexalobular form defined by alternating circular depressions and circular peaks, each circular depression defined by a same depression radius and each circular peak define by a same peak radius, said hexalobular form allowing an inclination of between 0° and 35° for the application of a tightening torque on a screw for the dynamic pillar for dental implantology; and
wherein the hexalobular form has a maximum external diameter (DE) from 1.3 mm to 2.4 mm, a maximum internal diameter (DI) in a range of 1.0 to 2.0 mm, radius of the depression (RCD) in a range of 0.15 to 0.35 mm, and a radius of the peak (RCC) in a range of 0.15 to 0.35 mm, and wherein the screwdriver has a total height (ATC) in a range of 18 to 35 mm.

5. An assembly for dental implantology, comprising a base (B) for coupling to the end of an implant; a guide tube (T) which comprises a body (T-1) and a screw (P) which comprises a head (P-1) in cylindrical form and a body (P-2) with thread; wherein the head of the screw has an internal part (P-1-A) with a female hexalobular form with a circular center and six circular depressions and six circular peaks alternating on the periphery, each circular depression defined by a same depression radius and each circular peak define by a same peak radius, said hexalobular form allowing an inclination of between 0° and 35° for the application of the tightening torque by a screwdriver on the screw; and wherein, for each of the six circular depressions, a curve defining the circular depression is along the same depression radius and for each of the six circular peaks, a curve defining the circular peak is along the same peak radius;

wherein the head of the screw has an external diameter (DE-1) from 1.8 mm to 2.7 mm, a greater internal diameter (DIMA-1) from 1.3 to 2.4 mm, a smaller internal diameter (DIME-1) from 1.0 to 2.0 mm, and an internal height (A1-1) from 0.5 to 1.5 mm; and wherein the depression radius is from 0.15 to 0.35 mm and the peak radius is from 0.15 to 0.35 mm.

\* \* \* \* \*